United States Patent
Uhm

(10) Patent No.: US 8,574,502 B2
(45) Date of Patent: Nov. 5, 2013

(54) STERILIZATION EFFECTS OF ACIDIC OZONE WATER

(76) Inventor: Han Sup Uhm, Potomac, MD (US)

( * ) Notice: Subject to any disclaimer, the term of this patent is extended or adjusted under 35 U.S.C. 154(b) by 0 days.

(21) Appl. No.: 13/507,649

(22) Filed: Jul. 17, 2012

(65) Prior Publication Data

US 2013/0011306 A1    Jan. 10, 2013

(51) Int. Cl.
C01B 6/00    (2006.01)
C02F 1/00    (2006.01)

(52) U.S. Cl.
USPC ........................................ 422/162; 210/747.5

(58) Field of Classification Search
USPC ........................................ 422/162; 210/747.5
See application file for complete search history.

(56) References Cited

U.S. PATENT DOCUMENTS 5,858,430 A * 1/1999 Endico .......................... 426/241

FOREIGN PATENT DOCUMENTS

JP    01051071 A   *   2/1989

* cited by examiner

*Primary Examiner* — Kevin Joyner
(74) *Attorney, Agent, or Firm* — The PL Law Group, PLLC

(57) ABSTRACT

This invention is directed to a sterilization method of contaminated areas with biological agents by making use of the acidic ozone water that very effectively kills spores of *Bacillus atrophaeus*, thereby demonstrating the capability of sterilizing a large surface-area in a very short time and reinstating the contaminated environment as free from toxic biological agents. The effective sterilization of the acidic ozone water is due to synergic benefits derived from the combination of ozone and acidity. The acidic ozone water can also effectively kill other ordinary microbes of viruses, bacteria, and fungi, hence being applicable to agriculture, seafood and livestock industries for the preservation of various products as well as being useful in hospitals or other germ infested areas for disinfections. Particularly, the acidity and ozone in the seawater sterilize microbes effectively, demonstrating a potential for the sterilization of a large amount of seawater in a short time. After the decontamination process, the acidic ozone water disintegrates into water and oxygen without any trace of harmful materials to the environment.

4 Claims, 4 Drawing Sheets

STERILIZATION EFFECTS OF ACIDIC OZONE WATER

REFERENCE CITED

U.S. Patent Documents

Figure 1:
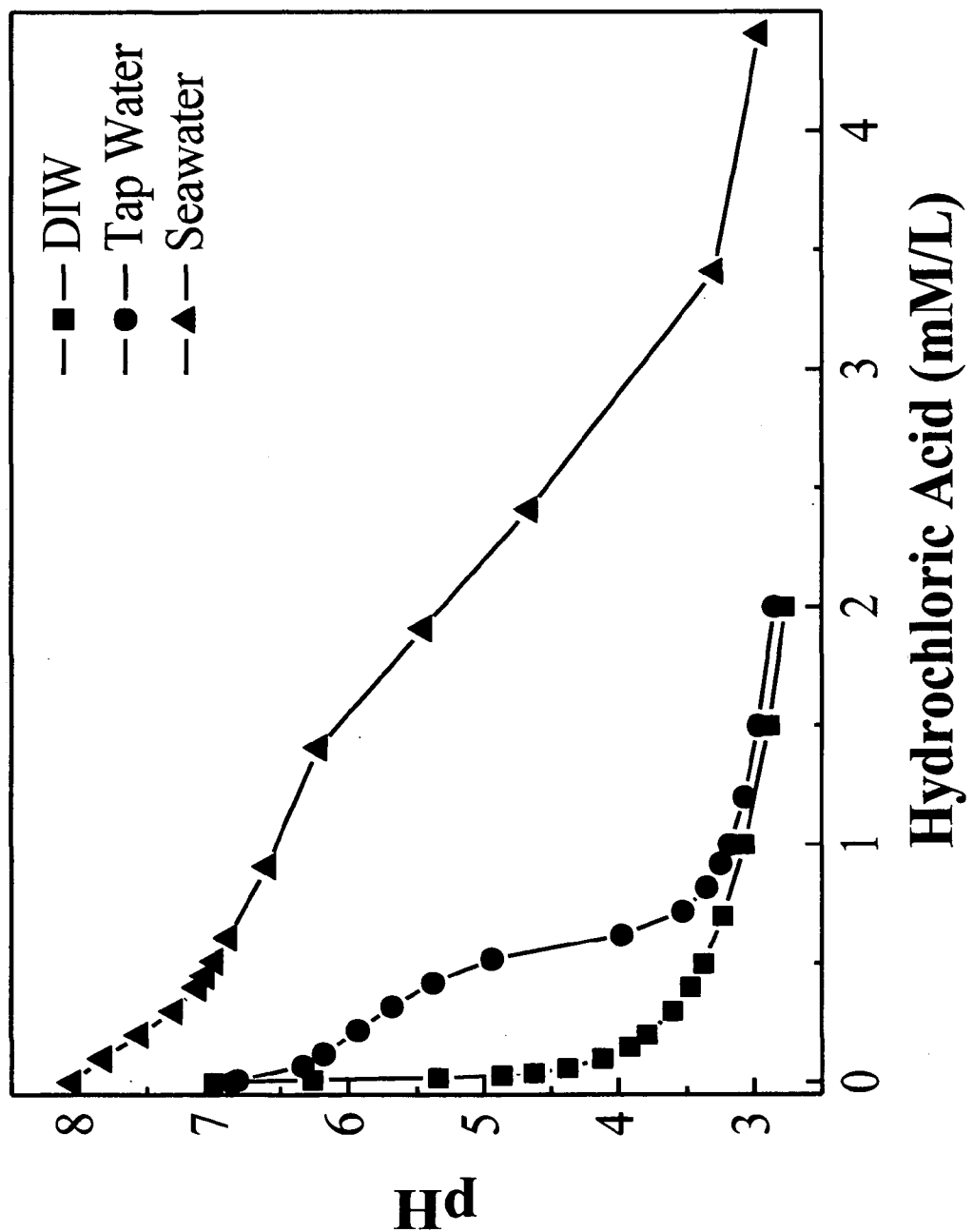

| | | |
|---|---|---|
| 5,983,909 | 11/1999 | Oh Eui Yeol et al |
| 6,506,428 B1 | 1/2003 | Berge et al |

FIELD OF THE INVENTION

The present invention relates generally to the disinfection of microbes including viruses, bacteria and fungi, but particularly, for the process of sterilizing biological warfare agents contaminating vast regions in the event of a release of agents in the environment, civilians or facilities. The biological warfare contaminants are eliminated by their exposure to the acidic ozone water. The present invention also shows that the acidity and ozone in the seawater sterilize microbes effectively, demonstrating a potential for the sterilization of a large amount of seawater in a short time.

BACKGROUND OF THE INVENTION

Biological warfare agents if released pose a great harm to mankind. Biological warfare agents including bacterial endospores like *Bacillus anthracis*, vegetative bacterial cells like *Vibrio cholera* and viruses like smallpox have been used in the past and will also be used in future military conflicts between nations and terrorists. Particularly, there were several incidents of bioterrorism in the fall of 2001 after the events of September 11, when preparations of *Bacillus anthracis* were mailed to public and private institutions, leading to 5 deaths and having a profound effect on the national psyche. The cost of decontamination and remediation of these attacks was very high. The main decontamination processes of these *anthracis* attacks were stripping and fumigation using chlorine dioxide, which is a toxic substance.

Elimination of unwanted microbes in seawater may be very useful in the shipping and fish-farming industries. World coastlines are contaminated by foreign biological species from ships' ballast water, disturbing local ecological systems. For example, copepods, native to Japan, China and Korea, appeared first in the Colombia River in 1990 have now spread to all of the west coast rivers in North America, displacing native copepods. European mussels brought by ships invaded the five great lakes in the US, causing great damage to hydroelectric power plants and factories. According to the US Coast Guard, the US spent more than 1 billion dollars to rectify this situation. In fact, the world sterilization cost of the pollution caused by ballast water is approximately 10 billion dollars annually. The International Maritime Organization decided that ballast water must be sterilized before discharging in order to prevent the spreading of foreign biological species and to protect the local ecological system. The fish-farming industries use various chemicals to kill bacteria, viruses and fungi, and these chemicals can harm fish populations and human. One of the notorious chemicals used in fish-farming industry is Malachite green, a carcinogenic material. Sterilizing unwanted microbes in seawater without the use of toxic chemicals is required.

Ozone is very effective in sterilizing microbes. Ozone after sterilization disintegrates into oxygen without leaving any harmful materials to environment. The difficulties associated with ozone are its finite lifetime in water and efficiency. In this context, properties of ozone in water have been investigated. Particularly, the ozone decay time in water was measured for a broad range of physical parameters including several values of ethanol concentration and different pH values. The increase of ozone decay time by lowering the pH value of the water was observed. It was also noted that the decay time decreases drastically as the ethanol concentration increases.

Assuming that N represents the microbe number in unit volume, the number of microbes killed per unit time and unit volume by acidic ozone water can be represented by $$\frac{dN}{dt} = -N\left[\alpha n_{O3} \exp\left(-\frac{t}{\tau}\right)\right], \quad (1)$$

where $n_{O3}$ is the initial ozone density, and $\alpha$ is the inactivation coefficient of ozone in units of L/(mg·s). Ozone ($\alpha n_{O3}$) in acidic ozone water in Eq. (1) inactivates the microbes. Integration of Eq. (1) over time t gives the density of microorganisms in terms of time t:

$$\log\left(\frac{N(t)}{N_0}\right) = -0.43\alpha n_{O3}\tau[1 - \exp(-t/\tau)], \quad (2)$$

where the constant $N_0$ represents the initial density of microorganisms. As can be seen from the theoretical model in Eq. (2), the concentration ($n_{O3}$) of ozone and its decay time ($\tau$) are the critically important factors on the sterilization. Increase of the ozone decay time ($\tau$) enhances the sterilization effects. The theoretical model developed in Eq. (2) for sterilization of microbes by ozone in water indicates that the main synergic effect of the acidity in water is the increase of the ozone decay time at a low pH value, thereby effectively killing endospores of *Bacillus atrophaeus*, demonstrating a potential for sterilization of microbes on a large contaminated area in a very short time and reinstating the contaminated environment as free from biological agents.

The purpose of the present invention is to develop a rapid and effective eliminating method of toxic biological warfare agents from large contaminated areas in the event of a release of agents on the environment, civilians or facilities. The acidic ozone water (AOW) can be produced abundantly in various forms like solutions, foams with substances, as well as mist and fog to satisfy a wide variety of operational objectives and can be retrofitted into many existing decontamination apparatus. The ozone in the acidic ozone water decays reasonably fast into oxygen without any trace after the decontamination process. The acidic water after the decontamination process can also be neutralized without any burden to the environment. Therefore, the acidic ozone water may be a good candidate for a mass sterilization of toxic biological warfare agents.

The acidic ozone water was proposed in the U.S. Pat. No. 5,983,909 issued to Oh Eui Yeol et. al. on Nov. 16, 1999. In that invention, an aqueous oxidizing acidic cleaning solution is produced by mixing an acidic solution with ozone water. An aqueous reducing acidic cleaning solution is produced by mixing an acidic solution with hydrogen water. The aqueous cleaning solution has effective cleaning power. Therefore, by selecting an appropriate aqueous cleaning solution according to the types of contaminants adhering to subjects during each manufacturing step, a plurality of types of contaminants can be removed by washing with this aqueous cleaning solution. On the other hand, the present invention makes use of synergic benefits derived from the combination of ozone and acidity in the acidic ozone water with a low pH value for sterilization of microbes instead of cleaning subjects.

The ozone and acidity in the acidic ozone water kill the microbes and then disintegrate into oxygen and ordinary water without leaving any trace of them as time goes by, thereby being harmless to the environment. The acidic ozone water therefore must be used to sterilize the contaminated area as soon as it is produced. This property is beneficial to the environment but limits applications of the acidic ozone water to broad areas because of ozone disintegration. Ozone dissociation in water is initiated by the negative OH ions, whose number increases faster with the pH value of the acidic water. For example, the ozone decay time ($\tau$) in the acidic ozone water with the pH value of 4 is about twice as long than that in ordinary fresh water with a pH value of 7. Therefore, it is much easier for a low pH value to make the ozonated water with high ozone concentration.

The ozone molecules disintegrate into oxygen molecules as they meet the negative OH ions or any other organic contaminants in water. The translational motion of the molecules in the water becomes faster as the water temperature increases. Ozone molecules have a higher chance of meeting the negative OH ions or other contaminants as the water temperature T increases. Accordingly, the ozone decay time $\tau$ in the acidic ozone water increases as the water temperature T decreases. The ozone in the acidic ozone water decays slowly if the water temperature is less than 4 degree Celsius. The chilled acidic ozone water preserves its properties long after its creation. The slowly decaying ozone molecules, before their disintegration, in the chilled acidic ozone water have a better chance of meeting and killing microbes.

Ice is the water crystal produced from freezing water. Ozone molecules, the positive hydrogen ions, the negative OH ions, and other contaminants in the acidic ozone ice are embedded inside the ice crystal. The positive hydrogen ions, whose density represents the acidity in the acidic ozone water, cannot move freely in ice, thereby preserving the ice acidity almost permanently. The ozone molecules in the acidic ozone ice are not allowed to meet the negative OH ions or any other contaminants in the ice, so that the ozone decay time $\tau$ becomes infinite in the acidic ozone ice. The ozonated ice was proposed in the U.S. Pat. No. 6,506,428 B1 issued to Berge and McClure on Jan. 14, 2003. In that invention, the ozonated ice was made for the disinfections of microbes by melting it as needed. The present invention extends the ozonated water concept in the previous U.S. Pat. No. 6,506,428 B1 to the acidic ozone water. The acidic ozone ice preserves its strong sterilizing-character permanently.

It is therefore an important object of the present invention to enhance the sterilizing strength of the acidic ozone water in order to achieve the elimination of toxic biological warfare agents in the contaminated area by exposing it to the ozone and acidity simultaneously in the acidic ozone water.

Another object of the present invention is to provide synergic benefits derived from the combination of ozone and acidity in the acidic ozone water for the sterilization of microbes on a large surface area contaminated by biological warfare agents.

One other object of the present invention is to provide synergic benefits derived from the combination of ozone and acidity in the acidic seawater for the sterilization of a large amount of seawater in a short time.

One additional object is to overcome the difficulties associated with the ozone decay in the acidic ozone water, and heretofore experienced in achieving efficient and rapid elimination of the toxic biological agents by chilling or freezing the acidic ozone water.

Additional objects, advantages and novel features of the invention will be explained in part in the following description, and will be apparent to those skilled in the following experiment.

SUMMARY OF THE INVENTION

The present invention is the method for the disinfections of microbes including viruses, bacteria and fungi with the acidic ozone water. Particularly, the present invention relates to a process for sterilizing biological warfare agents contaminating large surface areas in the event of a release of agents on the environment, civilians or facilities. The biological warfare contaminants are eliminated by their exposure to the acidic ozone water. The present invention also shows that the acidity and ozone in the seawater sterilize microbes effectively, demonstrating a potential for the sterilization of a large amount of seawater in a short time. Furthermore, the present invention provides the method of overcoming difficulties associated with the ozone decay in the acidic ozone water by chilling or freezing it.

The acidic water is made from neutral water by mixing acidic materials. Mixing a small amount of acid like hydrochloric acid (HCl) into water produces the acidic water. The acidity of the acidic water is represented by pH value. The neutral fresh water has pH value of 7. On the other hand, the natural seawater is slightly alkalic and has pH value of 8.2. The acidity of the acidic water increases as the pH value is lowered further down from 7 for fresh water or from 8.2 for seawater. The pH value of the acidic water was measured in terms of the mixing ratio of the hydrochloric acid. FIG. 1 is plots of the pH value versus the concentration of the hydrochloric acid in units of milli-mole per liter (mM/L) for three different waters, deionized water, tap water supplied from a municipal water supply system and seawater. The square dots represent the acidity of the acidic water from deionized water, circular dots represent the acidity of the acidic water made from the tap water, and triangular dots represent the acidity of the acidic seawater. Note in FIG. 1 that the pH value of the neutral seawater without any concentration of the acid is pH=8.2. The pH value of the acidic waters in FIG. 1 decreases as the concentration of the hydrochloric acid increases, thereby enhancing the acidity. The pH value in the acidic seawater has very peculiar profile in terms of the concentration of the hydrochloric acid. This peculiar property may be caused by various ions existing in the seawater, including sodium and chlorine ions. One ton of acidic water with its pH value of 4 made from tap water as represented by circular dots in FIG. 1 may require 0.6 mole of the hydrochloric acid, which is equivalent to 22 grams of the acid. Obviously a very small amount of acid is needed for making the acidic water from a tap water. The acidity of pH value of 4 is similar to the cola acidity and is also used for baby skin care. It is also noted from FIG. 1 that one ton of acidic seawater with its pH value of 6 made from seawater may require 1.5 mole of the hydrochloric acid, which is equivalent to 55 grams of the acid. Obviously a very small amount of acid is also needed for making the acidic seawater from plain seawater. One liter of seawater contains 35 grams of salt, which is equivalent to 0.54 moles. Thus, the mole fraction of the hydrochloric acid to the salt concentration in the acidic seawater with its pH=6 is 0.0027, which is negligibly small.

An ozone generator of corona discharge type produces a high ozone concentration gas, which is injected into a porous ceramic diffuser submerged into the acidic water that generates acidic ozone water (AOW). The ozone gas can also be dissolved into the acidic water by an ozone mixture device based on the Bernoulli effects, which mixes tiny bubbles of ozone gas with the water, dissolving about 60 percent of ozone into water. The dissolved ozone concentration in AOW is in the range of 0.1~100 milligrams per liter (mg/L) measured by an ultra violet spectroscopy.

Biological warfare agents like viruses or bacteria attach themselves to organic or inorganic aerosols and are spread when aerosol particles float around, eventually settling on surfaces of various objects with abundant organic compounds. Most of the ozone molecules in the acidic ozone water have disappeared due to the interaction with organic compounds in the vicinity of microbes. Only a fraction of ozone in the acidic ozone water participates in the killing activity of biological warfare agents. In this context, the ozone concentration in the acidic ozone water must be considerably higher than expected and the pH value of the acidic water must be significantly lower for the sterilization of contaminated areas with biological warfare agents. In other words, the ozone decay time τ and killing rate associated with acidity in the environment of abundant organic compounds in the real world are much less than the expected values in a controlled experiment without organic contaminations. The acidic ozone water can be sprayed over a large surface area contaminated with biological warfare agents. The acidic ozone water can also effectively kill other ordinary microbes of viruses, bacteria, and fungi, hence being applicable to agriculture, seafood and livestock industries for the preservation of various products as well as being useful in hospitals or other germ infested areas for disinfections. Furthermore, the ozone in the acidic seawater sterilizes very effectively a large amount of seawater in a short time.

BRIEF DESCRIPTION OF DRAWING FIGURES

A more complete appreciation of the invention and many of its attendant advantages will be aided by reference to the following detailed description in connection with the accompanying drawings:

FIG. 1 is plots of the pH value versus the concentration of the hydrochloric acid in units of milli-mole per liter (mM/L) for three different waters, deionized water, tap water supplied from a municipal water supply system and seawater. The square dots represent the acidity of the acidic water from deionized water, circular dots represent the acidity of the acidic water made from the tap water, and triangular dots represent the acidity of the acidic seawater.

Figure 2:
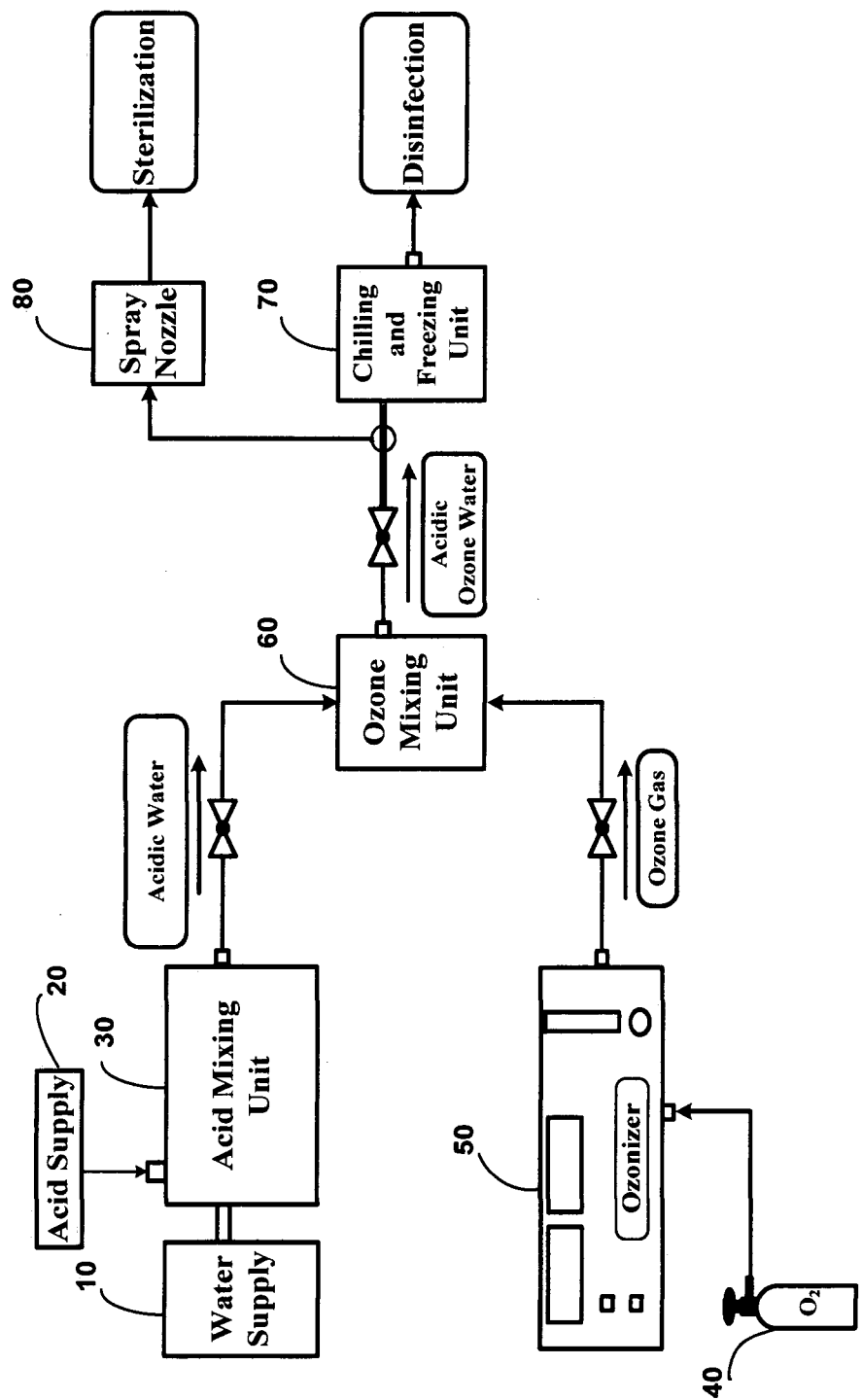

FIG. 2 is a block diagram illustrating the method of sterilizing microbes of the present invention.

Figure 3:
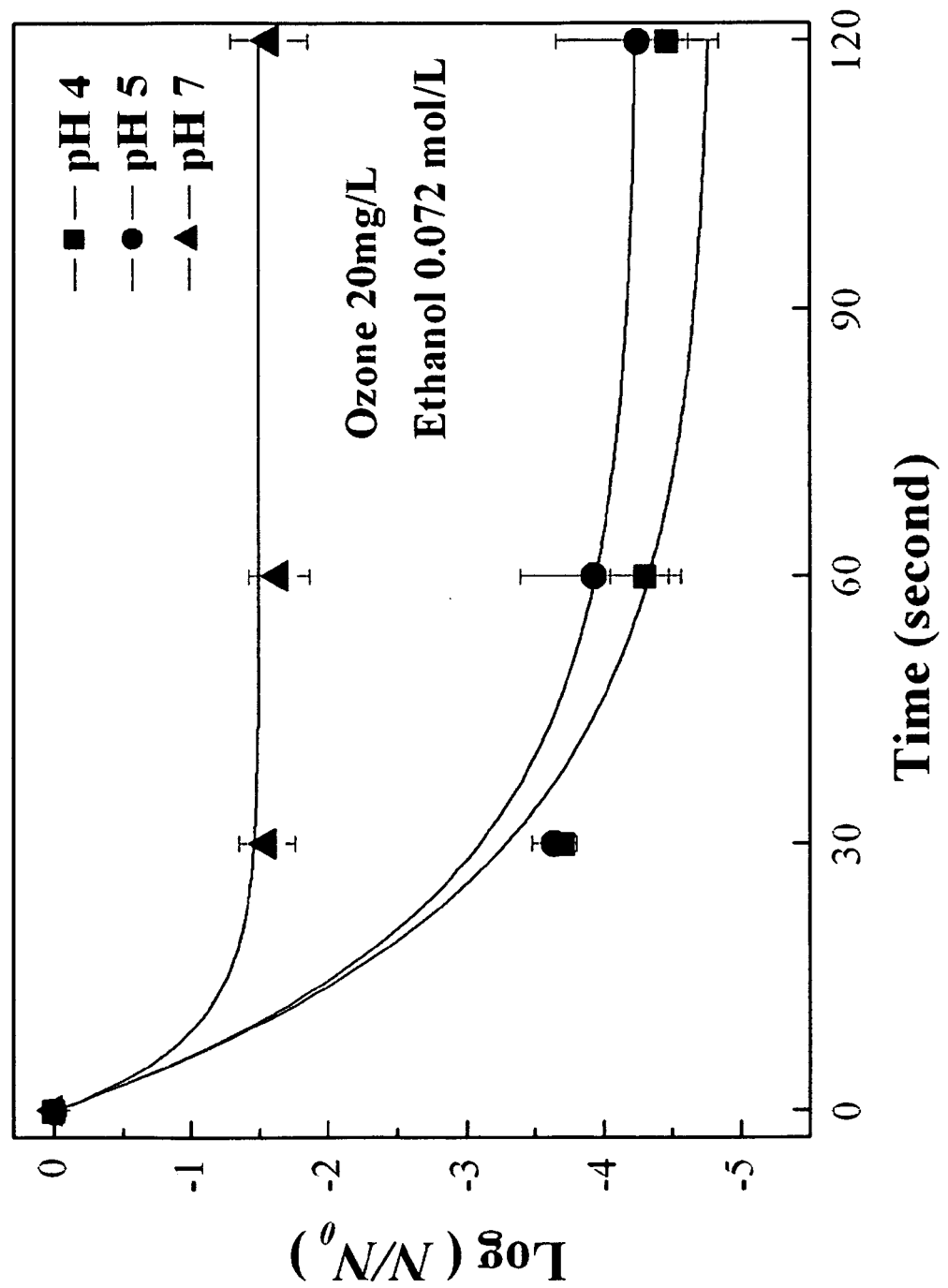

FIG. 3 is plots of the survival curves for *B. atrophaeus* endospores exposed to bactericidal formulation, AOW, with the pH value of 4, 5, and 7 for ethanol concentration of 0.072 mole/L. The vertical axis is the log of the ratio of the number of viable spores remaining (N) to the control number of $N_0$. Dots are experimental data and curves are obtained theoretically from Eq. (2).

Figure 4:
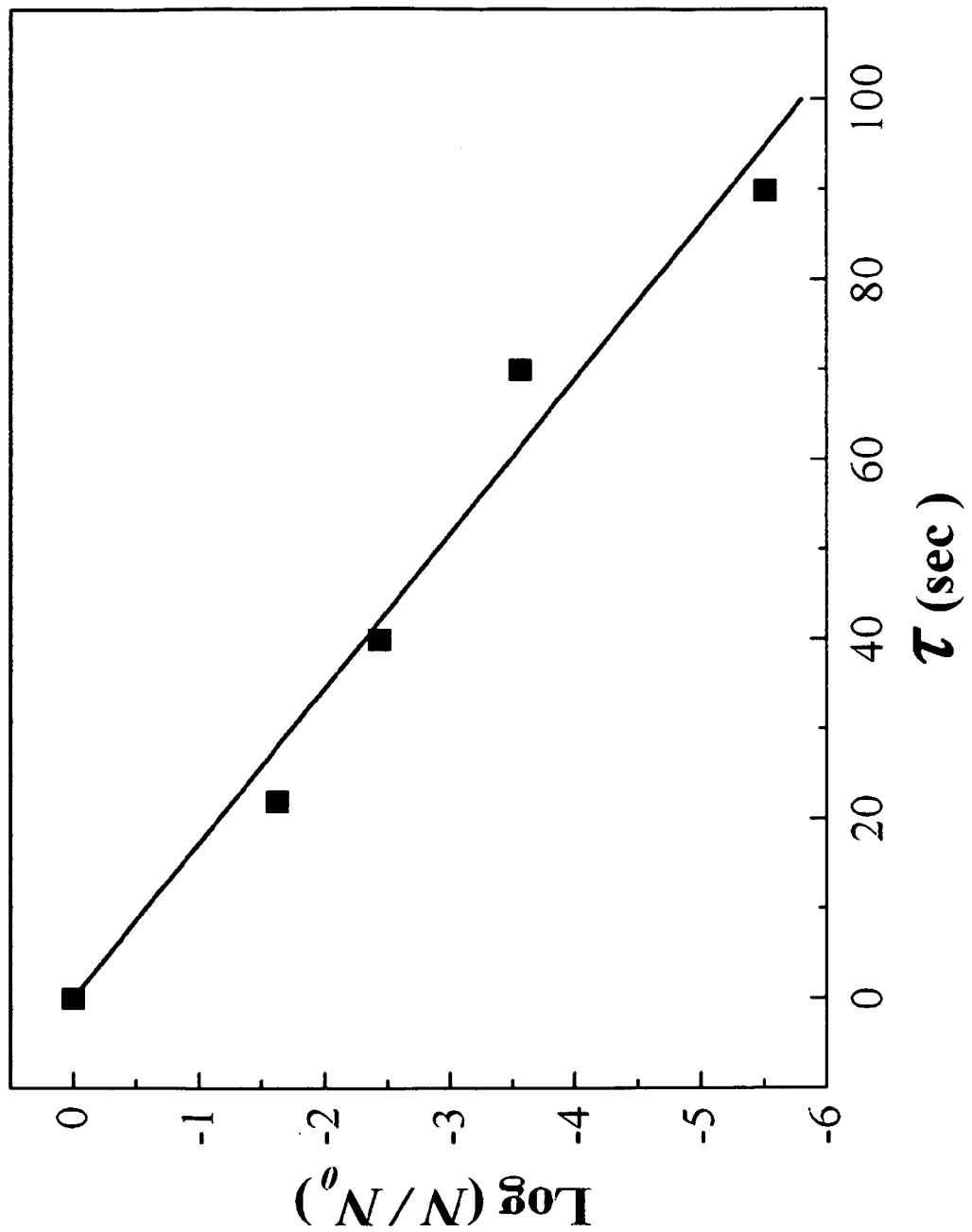

FIG. 4 is plots of the survival curve for *B. atrophaeus* endospores exposed to seawater with a 5 mg/L ozone concentration at several different pH values. The horizontal scale represents the ozone decay time τ measured in seconds corresponding to the specific pH value of seawater contaminated by an ethanol concentration of 7.7 mM/L.

DETAILED DESCRIPTION

The present invention is the method for disinfections of microbes including viruses, bacteria and fungi with the acidic ozone water. Particularly, the present invention relates to an apparatus and process for sterilizing biological warfare agents contaminating large surface areas in the event of a release of agents on the environment, civilians or facilities. The present invention also relates to an apparatus and process for sterilizing microbes in a large amount of seawater. The principles and operation of the method for disinfections of microbes of the present invention are described according to the drawings.

Referring now to the drawing in details, FIG. 2 diagrams water supply 10 and acid supply 20 that provide water and acid to the acid mixing unit 30, mixing the acid into water and generating the acidic water. The acidic water from the acid mixing unit 30 enters the ozone mixing unit 60. The ozone generator 50 converts oxygen from an oxygen tank 40 or an air compressor to an ozone-rich gas, which enters the ozone mixing unit 60. A typical ozone mixture device based on the Bernoulli effects mixes tiny bubbles of ozone gas with the water, dissolving about 60 percent of ozone into water. The ozone mixing unit 60 converts the acidic water to the acidic ozone water by dissolving ozone into acidic water. The spray nozzle 80 sprays the acidic ozone water over a large surface area contaminated with biological warfare agents, sterilizing the toxic warfare agents.

The acidic ozone water from the ozone mixing unit 60 can also be used for the disinfections of ordinary microbes of viruses, bacteria and fungi, which may cause the deterioration of products in agricultural, seafood and livestock industries. The acidic ozone water may be used for the sterilization of microbes in products from drug manufacturing industries. The acidic ozone water from the ozone mixing unit 60 can also be sprayed over farmlands or livestock sheds to control diseases by disinfecting disease-causing microbes. The acidic ozone water may also be useful in hospitals or other germ-infested areas for disinfections. The ozone and acidity in the acidic ozone water made from seawater also sterilize microbes in the seawater.

The acidic ozone water from the ozone mixing unit 60 enters the chilling and freezing unit 70 to be chilled or to be iced. The chilled acidic ozone water holds its ozone concentration and acidity for a long time after its production from the ozone mixing unit 60, thereby keeping its capability of sterilizing microbes for a long time. The acidic ozone ice from the chilling and freezing unit 70 preserves its ozone concentration permanently. The acidic ozone ice from an ice maker in the chilling and freezing unit 70 is distributed to one or more locations remote from the ice maker for sterilization or disinfections of microbes through routine ice delivery routes.

As mentioned earlier, a rapid and effective elimination of toxic biological warfare agents from a large contaminated area is the key issue in life threatening situations. In this context, the acidic ozone water must be produced abundantly within a short period of time. The acidic water can be generated from a tap water supplied by a municipal water supply system. The acidic water can also be generated from seawater abundant in earth. A typical ozone generator 50 operated by 40 kilowatts can produce ozone for more than 2 kg per hour, which is enough for the production of 1000 lpm of the acidic ozone water with an ozone concentration of 20 mg/L. For example, 1000 lpm of the acidic ozone water with the pH value of 3.8 and the ozone concentration of 20 mg/L from a moderate AOW apparatus can be sprayed over a large infected area, sterilizing the biological warfare agents.

EXAMPLE 1

The focus of the sterilization study is mostly on the decontamination of bacterial endospores because they are recognized to be the most difficult microorganisms to kill. The decontamination experiment of the bacterial endospores was carried out by using spores of Bacillus atrophaeus (B. Subtilis var. niger, ATCC 9372). In order to observe the influence of organic compounds on the ozone concentration and its kill properties, the original bacillus-spore suspension was made of a high concentration (40% by weight) of ethanol, which is harmless to spores. The spore concentration of the original spore suspension was $10^7$~$10^8$ spores per milliliter (mL). The spore treatment experiments were conducted by adding 0.1 mL of spore suspension with 10 mL of the acidic ozone water with three different pH value of 4, 5 and 7. The acidic ozone water in this example is made of a tap water supplied from a municipal water supply system. The ozone concentration in AOW was 20 mg/L. The concentration of ethanol in 10 mL of AOW is calculated to be 0.072 mole/L. Ozone in water decayed very fast with this ethanol concentration.

One mL of the solution was obtained from each sample after a specified contact time and was diluted with 9 mL of distilled water. FIG. 3 shows the survival curves for B. atrophaeus endospores exposed to bactericidal formulation, AOW, with the pH value of 4, 5, and 7 for ethanol concentration of 0.072 mole/L. The vertical axis is the log of the ratio of the number of viable spores remaining (N) to the control number of $N_0$. Each point in FIG. 3 represents an average value of 3 data. The untouched control was also analyzed every time to get the average control number $N_0=2.5 \times 10^6$, corresponding to log $N_0=6.4$. The error bars in FIG. 3 were obtained from the square root of the second moment of data around its mean value at each contact time. The ozone in the acidic ozone water decayed faster within 1 minute with the decay time being less than 30 seconds due to ethanol contamination. Therefore, most of the killing action in the acidic ozone water occurred within 1 minute as expected. Keeping in mind $N_0=2.5 \times 10^6$, it is noted that most of the spores were killed within 2 minutes by contact of the acidic ozone water at low pH value.

The curves in FIG. 3 represent the log reduction of live microbes versus time t in seconds for the acidic ozone water, obtained from Eq. (2) for AOW, $n_{O3}=20$ mg/L, and $\tau=8.1$ s for pH=7, $\tau=23$ s for pH=5 and $\tau=26$ s for pH=4. These ozone decay times were measured values for the ethanol concentration of 0.072 mole/L. The parameter $\alpha=0.0215$ L/(mg·s) in obtaining curves here was the least-squares fitted to the experimental data (triangular dots) for pH=7 in FIG. 3. Note that the ozone decay time $\tau$ increases from z=8.1 s for pH=7, to $\tau=23$ s for pH=5 and $\tau=26$ s for pH=4 in AOW at the room temperature of 25° C. The short decay time $\tau=8.1$ s in AOW with pH=7 is for a situation in which the environment contains many organic compounds represented by ethanol concentration of 0.072 mole/L corresponding to 3.4 g/L. The ozone concentration of 20 mg/L is far less than the ethanol concentration. However, 20 mg/L ozone concentration is equivalent to $1.4 \times 10^{17}$ molecules/cm$^3$, which is much higher than the spore concentration in the order of $10^6$/cm$^3$. It is observed from FIG. 3 that the log of the ratio of N to $N_0$ for the acidic ozone water in experimental data agrees remarkably well with the theoretical curves.

EXAMPLE 2

The sterilization of microbes in seawater was carried out by using the ozone and acid in the seawater. The spore concentration of the original spore suspension was $10^5$~$10^6$ spores per mL. The spore-treatment experiments were conducted by adding 0.2 mL of spore suspension to 10 mL of seawater at a specified pH value and ozone concentration of 5 mg/L. The concentration of ethanol in the mixture of 0.1 mL of spore suspension and 10 mL of seawater was 7.7 mM/L. Ozone in the water decayed rapidly with this ethanol concentration. For example, the ozone decay time $\tau$ in the seawater with its ethanol concentration of 7.7 mM/L was measured to be $\tau=22$ s for pH=8, $\tau=40$ s for pH=7, $\tau=70$ s for pH=6 and $\tau=90$ s for pH=5. One mL of the solution was obtained from each sample after 40 minutes of contact time and was diluted with 9 mL of distilled water. The contact time t=40 minutes is much longer than the ozone decay time $\tau$ less than 2 minute for the case of high concentration of ethanol. Equation (2) is further simplified to $$\log\left(\frac{N(t)}{N_0}\right) = -0.43\alpha n_{O3}\tau \quad (2)$$

for t>>$\tau$ typical to the sterilization of microbes in seawater. FIG. 4 shows the survival curve for B. atrophaeus endospores exposed to seawater with a 5 mg/L ozone concentration at several different pH values. The horizontal scale represents the ozone decay time $\tau$ measured in seconds corresponding to the specific pH value of seawater contaminated by an ethanol concentration of 7.7 mM/L. The vertical axis is the log of the ratio of the number of viable spores remaining (N) to the control number of $N_0$. The untouched control was also analyzed each time to obtain the average control number $N_0=3.3 \times 10^5$, which corresponded to log $N_0=5.52$.

The dots in FIG. 4 represent the experimental data of the log reduction of live microbes versus the ozone decay time $\tau$ in seconds for seawater with an ozone concentration of 5 mg/L and contaminated by an ethanol concentration of 7.7 mM/L corresponding to 360 mg/L. In effect, all of the spores were killed at $\tau=90$ s, but one surviving spore at $\tau=90$ s was assumed for convenience regarding the log scale plot shown in FIG. 4. The molecular number of ethanol in this seawater is 150 times greater than that of ozone. The straight line in FIG. 4 was obtained from Eq. (3) and was linearly fitted to the experimental dots (squares) with the parameter $\alpha n_{O3}=0.135$/s, which was the least-squares value fitted to the experimental data in FIG. 4. Assuming an initial ozone concentration of $n_{O3}=5$ mg/L, the inactivation coefficient of ozone was calculated to be $\alpha=0.027$ L/(mg·s) for $\alpha n_{O3}=0.135$/s. The short decay time $\tau$ in FIG. 4 represents a situation in which the seawater contains many organic compounds. On the other hand, for relatively clean seawater in an application to ballast water, the organic material is less than 5 mg/L and the ozone decay time at pH=7 is 3.3 minutes. Equation (3) predicts the viable B. spore number of N=8 for $N_0=3.3 \times 10^5$ at an ozone concentration of $n_{O3}=2$ mg/L.

It is observed from FIG. 4 that the log of the ratio of N to $N_0$ for the acidic seawater in the experimental data is in good agreement with a theoretical model. The ozone decay time of $\tau=90$ s at pH of 5 is four times that at a pH of 8. Therefore, an increase of the ozone decay-time by lowering the pH value must play a pivotal role in the killing process. Similar sterilization may be achieved by a four-fold increase in the ozone concentration in seawater at pH=8. However, an ozone concentration of 20 mg/L in seawater may be impractical for application to sterilizations. Hence, a reasonable ozone concentration at a low pH value may make it possible to sterilize a large amount of seawater in relatively little time, freeing this water from unwanted microbes. FIG. 4 clearly demonstrates that an increase of the ozone decay time at a low pH has the most important synergic effect on the sterilization of microbes in seawater.

What is claimed is:

1. An apparatus for sterilizing microbes on a contaminated area and for sterilizing microbes in water, said apparatus comprising:
   a device for forming an ozone gas;
   an acid material supply unit containing acid material comprised of HCl;
   a mixing device for dissolving the acid material supplied from the acid material supply unit into water to produce an acidic water;
   a mixing device for dissolving said ozone gas into said acidic water to form an acidic ozone water;
   a device to spray said acidic ozone water on a contaminated area for sterilization of microbes; and
   a device for freezing said acidic ozone water to produce acidic ozone ice.

2. The apparatus according to claim 1, wherein said microbes are viruses, bacteria and fungi comprised of biological warfare agents, that cause the deterioration of products from agricultural, seafood and livestock industries, that cause diseases to farm crops and livestock, and that infest hospitals, products from drug manufacturing industries and areas prone to germs.

3. The apparatus according to claim 1, wherein said contaminate area is the area contaminated by said microbes.

4. The apparatus according to claim 1, wherein the acid material supply unit contains the acidic material consisting essentially of HCl.

* * * * *